United States Patent [19]

Cooper et al.

[11] Patent Number: 4,851,412
[45] Date of Patent: Jul. 25, 1989

[54] DIHYDROPYRIDINE ANTIALLERGIC AND ANTIINFLAMMATORY AGENTS

[75] Inventors: Kelvin Cooper, Ramsgate; Michael J. Fray, Wingham, Nr. Canterbury; Kenneth Richardson, Birchington, all of England

[73] Assignee: Pfizer Inc., New York, N.Y.

[21] Appl. No.: 198,020

[22] Filed: May 24, 1988

[30] Foreign Application Priority Data

May 30, 1987 [GB] United Kingdom ............... 8712747

[51] Int. Cl.$^4$ ..................... A61K 31/44; A61K 31/52; C07D 471/04; C07D 473/00
[52] U.S. Cl. .................................... 514/266; 514/300; 514/303; 544/277; 544/281; 546/118; 546/121
[58] Field of Search ............... 546/118, 121; 544/277, 544/281; 514/266, 300, 303

[56] References Cited

FOREIGN PATENT DOCUMENTS 100189  5/1986  European Pat. Off. .
0258033 3/1988  European Pat. Off. .
0266989 5/1988  European Pat. Off. .

Primary Examiner—Mary C. Lee
Assistant Examiner—Bernard J. Dentz
Attorney, Agent, or Firm—Peter C. Richardson; J. Trevor Lumb; James M. McManus

[57] ABSTRACT

Compounds of the formula:

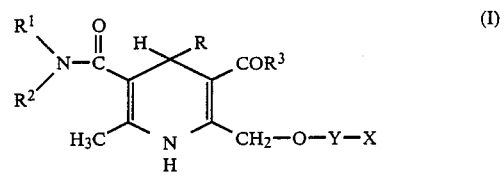

where R is substituted phenyl, $R^1$ is alkyl or pyridyl, $R^2$ is hydrogen, $R^3$ is alkoxy, alkylamino, hydroxy or benzyloxy, Y is alkylene and X is heterocyclic as antiallergic and antiinflammatory agents.

6 Claims, No Drawings

DIHYDROPYRIDINE ANTIALLERGIC AND ANTIINFLAMMATORY AGENTS

BACKGROUND OF THE INVENTION

This invention relates to dihydropyridines, specifically to certain 4-aryl-5-carbamoyl-1,4-dihydropyridines which are useful in the treatment of allergic and inflammatory conditions in humans and animals.

A number of 1,4-dihydropyridines have been previously described as antiischaemic and antihypertensive agents. These compounds are able to inhibit the movement of calcium into cells and are thus active in the treatment or prevention of a variety of cardiac conditions or as antihypertensive agents. (See for example EP-A-No. 100189.) However the compounds of the present invention are potent and selective antagonists of platelet activating factor and as such they have clinical utility in a quite different area, namely for treating allergic and inflammatory conditions such as asthma and arthritis respectively.

Platelet activating factor (PAF), 1-O-alkyl--2-acetyl-sn-glyceryl-3-phosphorylcholine) is an ether phospholipid whose structure was first elucidated in 1979. It is produced by, released from and interacts with many pro-inflammatory cells, platelets and the kidney. In addition to potent platelet aggregating activity, PAF exhibits a wide spectrum of biological activities elicited either directly or via the release of other powerful mediators such as thromboxane $A_2$ or the leukotrienes. In vitro, PAF stimulates the movement and aggregation of neutrophils and the release therefrom of tissue-damaging enzymes and oxygen radicals. These activities contribute to actions of PAF in vivo consistent with it playing a significant role in inflammatory and allergic responses. Thus, intradermal PAF has been shown to induce an inflammatory response, with associated pain, accumulation of inflammatory cells and increased vascular permeability, comparable with the allergic skin reaction following exposure to allergen. Similarly, both the acute broncho-constriction and chronic inflammatory reactions elicited by allergens in asthma can be mimicked by intratracheal administration of PAF. Accordingly agents which antagonise the actions of PAF and, consequently also prevent mediator release by PAF, will have clinical utility in the treatment of a variety of allergic and inflammatory conditions such as asthma and arthritis, respectively.

In addition to the above, PAF has been implicated as being involved in a number of other medical conditions. Thus in circulatory shock, which is characterised by systemic hypotension, pulmonary hypertension and increased lung vascular permeability, the symptoms can be mimicked by infusion of PAF. This coupled with evidence showing that circulating PAF levels are increased by endotoxin infusion indicate that PAF is a prime mediator in certain forms of shock. Intravenous infusion of PAF at doses of 20-200 pmol kg$^{-1}$ min$^{-1}$ into rats results in the formation of extensive haemorrhagic erosions in the gastric mucosa and thus PAF is the most potent gastric ulcergoen yet described whose endogenous release may underlie or contribute to certain forms of gastric ulceration. Psoriasis is an inflammatory and proliferative disease characterised by skin lesions. PAF is pro-inflammatory and has been isolated from lesioned scale of psoriatic patients indicating PAF has a role in the disease of psoriasis. And finally, increasing evidence supports a potential pathophysiological role for PAF in cardiovascular disease. Thus recent studies in angina patients show PAF is released during atrial pacing and, in pigs, intracoronary injection of PAF induces a prolonged decrease in coronary flow while in guinea pig hearts it induces regional shunting and ischaemia. PAF has also been shown to initiate thrombus formation in a mesenteric artery preparation both when administered exogenously and when released endogenously. More recently PAF has been shown to play a role in brain ischaemia induced in animal models of stroke.

Thus compounds of the invention, by virtue of their ability to antagonise the actions of PAF, could well be of value in the treatment of any of the above conditions.

SUMMARY OF THE INVENTION

According to the present invention there are provided compounds of the formula

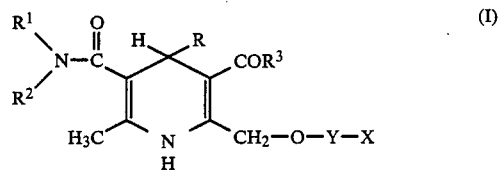

or a pharmaceutically acceptable salt thereof, wherein R is 2-chlorophenyl, 2-bromophenyl or 2-methylthiophenyl; $R^1$ is pyridyl or alkyl of one to four carbon atoms; $R^2$ is hydrogen; $R^3$ is alkoxy of one to four carbon atoms, benzyloxy, hydroxy or alkylamino of one to four carbon atoms; Y is ethylene or propylene; and X is 1-, 2-, or 3-imidazopyridyl or 1-, 2-, or 3-imidazopyrimidyl optionally substituted by methyl.

Preferred among these compounds are those where R is 2-chlorophenyl, $R^2$ is hydrogen, $R^3$ is alkoxy of one to four carbon atoms and Y is ethylene. Especially preferred within this group are the compounds where $R^1$ is t-butyl, $R^3$ is ethoxy and X is 2-methyl-1-imidazo[4,5-c]pyridyl and where $R^1$ is 2-pyridyl, $R^3$ is ethoxy and X is 2-methyl-1-imidazo[4,5-c]pyridyl.

The present invention also comprises a method for treating an inflammatory or allergic condition in a mammal which comprises administering to said mammal an antiinflammatory or antiallergic effective amount of a compound selected from those of the present invention.

The present invention also relates to a pharmaceutical composition which comprises a unit dosage form of a compound of the present invention together with a pharmaceutically acceptable diluent or carrier.

The imidazopyridine or imidazopyrimidine group X may be attached to Y at the 1-, 2- or 3-position. The position of ring fusion can also vary to include imidazo[4,5-b]pyridine, imidazo[4,5-c]pyridine, imidazo[1,2-a]pyridine, imidazo[4,5-d]pyrimidine, imidazo[1,2-c]pyrimidine and imidazo[1,2-b]pyrimidine derivatives. The group may be substituted in either or both of the fused rings by one or more of the substituents previously defined.

The compounds of the formula (I) containing asymmetric centres will exist as one or more pairs of enantiomers, and such pairs or individual isomers may be separable by physical methods, e.g. by fractional crystallisation or chromatography of the parent compounds or of a suitable salt or derivatives thereof. The invention includes all the enantiomers whether separated or not.

The pharmaceutically acceptable acid addition salts of the compounds of the formula (I) which form such salts are those formed from acids which form non-toxic acid addition salts, for example the hydrochloride, hydrobromide, sulphate or bisulphate, phosphate or acid phosphate, acetate, citrate, fumarate, gluconate, lactate, maleate, succinate, tartrate, methanesulphonate, benzenesulphonate and p-toluenesulphonate salts.

The compounds of formula I may be obtained by the Hantzsch synthesis, according to the following reaction scheme:

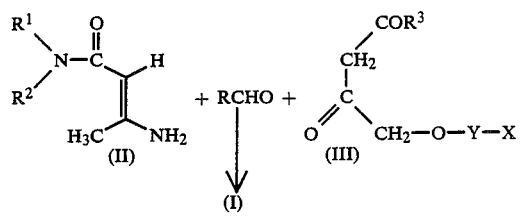

wherein R, $R^1$, $R^2$, $R^3$, Y and X are as previously defined.

In a typical procedure, the ketoester or ketoamide (III) and aldehyde are heated under reflux in a suitable organic solvent, e.g. a $C_1$-$C_4$ alkanol such as ethanol, for about 15 minutes, and then the amino-crotonamide (II) is added. Alternatively, the aminocrotonamide (II), the ketocompound (III) and the aldehyde can be heated together in the solvent. Optionally a small amount of a lower alkanoic acid such as acetic acid is added to neutralise the solution. The resulting solution can then be heated at 60°–130° C., preferably under reflux, until the reaction is essentially complete, typically in 24 hours or less. The product of the formula (I) can then be isolated and purified by conventional procedures, for example by partition, recrystallisation or by chromatography.

Certain compounds of formula (I) are also conveniently obtained by means of simple chemical transformation reactions. Thus for example compounds of formula (I) wherein $R^3$ is benzyloxy may be subjected to a conventional catalytic hydrogenation to yield the corresponding compounds wherein $R^3$ is OH. The acid product may then be reacted with ammonia or with an amine in the presence of a diimide coupling agent, to yield the amide or substituted amide wherein $R^3$ is $NR^4R^5$. Appropriate reagents and conditions for these transformations will be well known to those skilled in the art.

The ketoesters and ketoamides of formula (III) can be prepared by methods analogous to those of the prior art, such as the method described in European Pat. No. 100189 which is essentially the method of Troostwijk and Kellogg, J.C.S. Chem. Comm., 1977, page 932, or as described in the Preparations given hereafter. Similarly the amino-crotonamides (II) are either known compounds or can be prepared by conventional procedures, for example from the ketoamide by reaction with ammonia. Also the aldehydes RCHO are either known or can be prepared by known methods in accordance with literature precedents.

The activity of the compounds of the invention is shown by their ability to inhibit the platelet aggregating activity of PAF in vitro. Testing is performed as follows:

Blood samples are taken from either rabbit or man into 0.1 vol disodium ethylenediamine tetraacetic acid buffer and the samples centrifuged for 15 minutes to obtain platelet rich plasma. The plasma is further centrifuged to give a platelet pellet which is washed with a buffer solution (4 mM $KH_2PO_4$, 6 mM $Na_2HPO_4$, 100 mM NaCl, 0.1% glucose and 0.1% bovine serum albumin, pH 7.25) and finally resuspended in buffer solution to a concentration of $2\times10^8$ platelets/ml. A sample (0.5 ml) is pre-incubated for two minutes at 37° C. in a Paton aggregometer, either with vehicle alone, or with vehicle containing the particular compound under test. PAF is added at a sufficient concentration to give a maximum aggregating response in the absence of test compound ($10^{-8}$ to $10^{-9}$ molar), and the platelet aggregation is measured by following the increase in light transmission of the solution. The experiment is repeated in the presence of test compound at a range of concentrations and the concentration of compound required to reduce the response to 50% of its maximum value is recorded as the $IC_{50}$ value.

The activity of the compounds of formula (I) is also demonstrated in vivo by their ability to protect mice from the lethal effect of an injection of PAF. A mixture of PAF (50 μg/kg) and DL-propanolol (5 mg/kg) in 0.9% w/v sodium chloride is injected (0.2 ml) via a tail vein into mice. The compounds under test are either injected into the tail vein immediately prior to the PAF/propanolol injection or administered orally by gavage two hours earlier. The compounds are tested at several doses in groups of 5 mice and the dose which reduces mortality to 50% is recorded as the $PD_{50}$ value.

The compounds are also tested for their ability to reduce PAF-induced bronchoconstriction in anaesthetised guinea pigs. In this test airways resistance and dynamic lung compliance are calculated from recordings of airflow and transpleural pressure and calculation of tidal volume. The bronchoconstriction induced by PAF (100 ng/kg) is determined. One hour after the initial dose of PAF the compound under test is administered and the test repeated. The ability of the compound to reduce the bronchoconstrictor effect of PAF is recorded as a ratio.

For therapeutic use the compounds of the formula (I) will generally be administered in admixture with a pharmaceutical carrier selected with regard to the intended route of administration and standard pharmaceutical practice. For example, they may be administered orally in the form of tablets containing such exipients as starch or lactose, or in capsules or ovules either alone or in admixture with excipients, or in the form of elixirs or suspensions containing flavouring or colouring agents. They may be injected parenterally, for example, intravenously, intramuscularly or subcutanesouly. For parenteral administration, they are best used in the form of a sterile aqueous solution which may contain other substances, for example, enough salts or glucose to make the solution isotonic with blood.

For administration to man in the curative or prophylactic treatment of allergic bronchial conditions and arthritis, oral dosages of the compounds will generally be in the range of from 2–1000 mg daily for an average adult patient (70 kg). Thus for a typical adult patient, individual tablets or capsules contain from 1 to 500 mg of active compound, in a suitable pharmaceutically acceptable vehicle or carrier. Dosages for intravenous administration would typically be within the range 1 to 10 mg per single dose as required. For the treatment of allergic and bronchial hyper-reactive conditions, inhalation via a nebuliser or aerosol may be the preferred route of drug administration. Dose levels by this route would be within the range 0.1 to 50 mg per single dose as required. In practice the physician will determine the actual dosage which will be most suitable for an individual patient and it will vary with the age, weight and response of the particular patient. The above dosages are exemplary of the average case but there can, of course, be individual instances where higher or lower dosage ranges are merited, and such are within the scope of this invention.

Thus in a further aspect the invention provides a pharmaceutical composition comprising a compound of the formula (I), or a pharmaceutically acceptable salt thereof, together with a pharmaceutically acceptable diluent or carrier.

The invention also includes a compound of the formula (I), or a pharmaceutically acceptable salt thereof, for use in medicine, in particular in the treatment of allergic and inflammatory conditions in a human being.

The preparation of the compounds of the invention is further illustrated by the following Examples.

EXAMPLE 1

4-(2-Bromophenyl)-5-(N-t-butylcarbamoyl)-3-isopropoxycarbonyl-6-methyl-2-[2-(2-methyl-1-imidazo[4,5-c]pyridyl)ethoxymethyl]-1,4-dihydropyridine (a) 2-Methyl-1-(2-hydroxyethyl)-imidazo[4,5-c]pyridine (5 g, 28.5 mmole) was added to a suspension of sodium hydride (60% oil dispersion, 2.3 g, 57 mmole) in dry tetrahydrofuran (100 ml) and the mixture was sonicated for 2 hours at room temperature. A solution of isopropyl 4-chloroacetoacetate (5.1 g, 28.5 mmole) in tetrahydrofuran (100 ml) was added dropwise under nitrogen with sonication and the mixture was sonicated for 5 hours at room temperature. 2N Hydrochloric acid (100 ml) was added and the tetrahydrofuran removed under reduced pressure. The aqueous solution was washed with methylene chloride (2×50 ml), neutralised with potassium carbonate and extracted with ethyl acetate (3×25 ml). The combined extracts were washed with water, dried over magnesium sulphate and evaporated. The residue was chromatographed on silica, eluting with ethyl acetate containing 10% isopropyl alcohol to yield isopropyl 4-[2-(2-methyl-1-imidazo[4,5-c]pyridyl)ethoxy]-3-ketobutanoate (5.3 g, 58%). Rf (silica; methanol, ethyl acetate 1:4) 0.13; N.M.R. (CDCl$_3$) δ=1.05 (d, J=6 Hz, 6H); 2.50 (s, 3H); 3.15 (s, 2H); 3.67 (t, J=5.5 Hz, 2H); 3.93 (s, 2H); 4.19 (t, J=5.5 Hz, 2H); 4.8 (m, 1H); 7.11-8.19 (m, 3H).

(b) The product from (a) above (319 mg, 1 mmole), 2-bromobenzaldehyde (185 mg, 1 mmole) and N-t-butyl-3-aminocrotonamide (160 mg, 1 mmole) were heated under reflux in isopropyl alcohol (10 ml) for 6 hours. The reaction mixture was evaporated to dryness under reduced pressure and the residue chromatographed on silica eluting with ethyl acetate containing 5% diethylamine to give the title product (0.18 g, 35%) m.p. 160°–165° C. Rf (silica; ethyl acetate, diethylamine 19:1) 0.18. Found: C, 59.32; H, 6.44; N, 11.31. $C_{31}H_{38}BrN_5O_4$ requires C, 59.61; H, 6.13; N, 11.21%.

EXAMPLES 2–5

The following compounds were prepared by the method of Example 1(b) starting with the ketoester of Example 1(a) and using either 2-chloro, 2-bromo or 2-methylthio-benzaldehyde and N-t-butyl-3-aminocrotonamide or N-(pyrid-2-yl)-3-aminocrotonamide as appropriate:

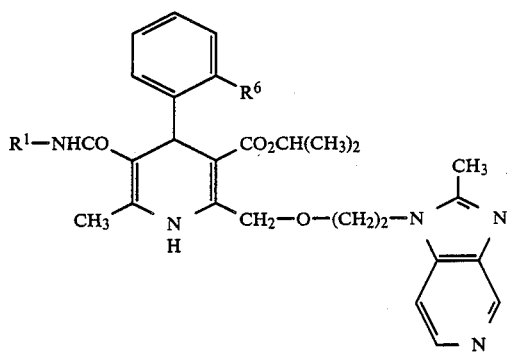

| Example No. | R$^1$ | R$^6$ | m.p. °C. | Analysis % (Theoretical in brackets) | | |
|---|---|---|---|---|---|---|
| | | | | C | H | N |
| 2 | (CH$_3$)$_3$C— | Cl | 158–163 | 61.32 (61.27 | 6.36 6.76 | 11.71 11.52) |
| 3 | pyrid-2-yl | Br | 155–165 | 59.21 (59.54 | 5.40 5.15 | 12.74 13.02) |
| 4 | pyrid-2-yl | Cl | 151–157 | 63.86 (63.95 | 5.48 5.50 | 13.77 13.99) |
| 5 | (CH$_3$)$_3$C— | SCH$_3$ | 162–168 | 64.68 (64.97 | 7.02 6.94 | 12.02 11.84) |

EXAMPLES 6–9

The following compounds were prepared by the method of Example 1 using as starting materials for Step (a) ethyl 4-chloroacetoacetate and the appropriate hydroxyalkylimidazopyridine (See Preparations 1–4), and reacting the ketoester product with 2-chlorobenzaldehyde and N-t-butyl-3-aminocrotonamide, as described in Example 1, Step (b).

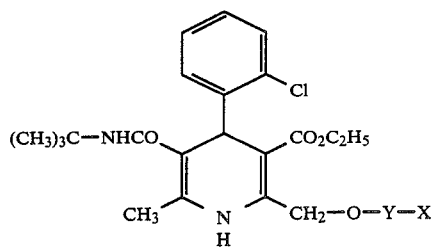

| Example No. | Y—X | m.p. °C. | Analysis % (Theoretical in brackets) C | H | N |
|---|---|---|---|---|---|
| 6 | —(CH₂)₂—N (imidazo[4,5-b]pyridine, 2-CH₃) | 167 | 63.65 (63.65 | 6.13 6.41 | 12.20 12.37) |
| 7 | —(CH₂)₂—N (imidazo[4,5-c]pyridine, 2-CH₃) | 167 | 63.36 (63.65 | 6.41 6.41 | 12.21 12.37) |
| 8 | —(CH₂)₂—N (imidazo[4,5-d]pyridine, 2-CH₃) | 173 | 63.38 (63.65 | 6.69 6.41 | 12.05 12.37) |
| 9 | —(CH₂)₃— (1-CH₃-imidazo[4,5-c]pyridine) | 188 | 63.30 *(63.20 | 6.65 6.67 | 12.16 11.89) |

*calculated for hemihydrate.

EXAMPLES 10–16

The following compounds were prepared by the method of Example 1 using as starting material for Step (a) ethyl 4-chloroacetoacetate and the appropriate hydroxyalkylimidazopyridine or hydroxyalkylimidazopyrimidine (see Preparations 1–7) and reacting the ketoester product with N-(pyrid-2-yl)-3-aminocrotonamide and 2-chlorobenzaldehyde as described in Example 1, Step (b).

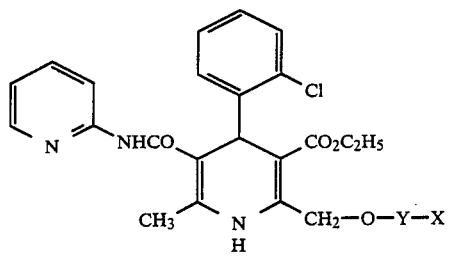
| Example No. | Y—X | m.p. °C. | Analysis % (Theoretical in brackets) | | |
|---|---|---|---|---|---|
| | | | C | H | N |
| 10 | —(CH$_2$)$_2$—N⟨imidazo[4,5-b]pyridine, 2-CH$_3$⟩ | 185 | 63.23 (63.42 | 5.26 5.32 | 13.92 14.32) |
| 11 | —(CH$_2$)$_2$—N⟨imidazo[4,5-c]pyridine, 2-CH$_3$⟩ | 158 | 63.73 (63.42 | 5.53 5.32 | 14.25 14.32) |
| 12 | —(CH$_2$)$_2$—N⟨imidazo[4,5-c]pyridine isomer, 2-CH$_3$⟩ | 207 | 63.32 (63.42 | 5.55 5.32 | 14.40 14.32) |
| 13 | —(CH$_2$)$_3$—⟨1-methylimidazo[4,5-c]pyridin-2-yl⟩ | 177 | 63.61 (63.94 | 5.59 5.53 | 13.84 13.98) |
| 14 | —(CH$_2$)$_2$—⟨3-methylimidazo[1,2-a]pyridin-2-yl⟩ | 166–7 | 65.18 (65.58 | 5.10 5.50 | 11.81 11.95) |
| 15 | —(CH$_2$)$_2$—N⟨imidazo[4,5-b]pyridine, 2-CH$_3$⟩ | 224–5 | 63.50 (63.42 | 5.59 5.32 | 14.01 14.32) |

-continued

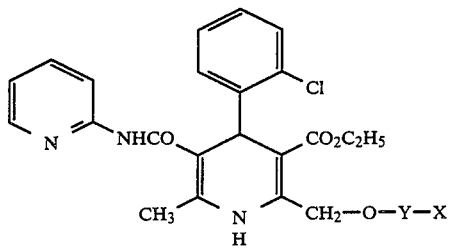

| Example No. | Y—X | m.p. °C | Analysis % (Theoretical in brackets) | | |
|---|---|---|---|---|---|
| | | | C | H | N |
| 16 | —(CH$_2$)$_2$—N⟨C(CH$_3$)=N—imidazopyridyl⟩ | 184–6 | 59.76 (59.45 | 5.21 5.32 | 15.99 16.18)* |

*calculated for hemihydrate.

EXAMPLE 17

3-Benzyloxycarbonyl-4-(2-chlorophenyl)-6-methyl-2-[2-(2-methyl-1-imidazo[4,5-c]pyridyl)ethoxymethyl]-5-[N-(2-pyridyl)carbamoyl]-1,4-dihydropyridine Ethyl 4-[2-(2-methyl-1-imidazo[4,5-c]pyridyl)ethoxy]butanoate (3.8 g) was stirred at reflux in a mixture of toluene (50 ml) and benzyl alcohol (26 ml) for 6 hours. The toluene was removed under reduced pressure and the resulting solution of benzyl 4-[2-(2-methyl-1-imidazo[4,5-c]pyridyl)ethoxy]-3-oxobutanoate (4.6 g) in benzyl alcohol (26 ml), was treated with 2-chlorobenzaldehyde (1.75 g) and N-(2-pyridyl)-3-aminocrotonamide (2.2 g). The mixture was stirred at 80° C. for 3 hours, and the benzyl alcohol was then removed under reduced pressure and the crude product chromatographed on silica eluting with a mixture of methanol and ethyl acetate (3:1). Fractions containing the desired product were combined and evaporated. The resulting foam was stirred in diethyl ether overnight, the ether removed and the product dried under vacuum to yield the title compound as a yellow solid. (2.71 g; 33%).

N.M.R. (CDCl$_3$) δ1.82 (s, 3H); 2.75 (s, 3H); 3.92 (t, J=4 Hz, 2H); 4.40 (t, J=4 Hz, 2H); 4.72 (d, J=8 Hz, 1H); 4.84 (d, J=8 Hz, 1H); 5.00 (d, J=10 Hz, 1H); 5.18 (d, J=10 Hz, 1H); 5.43 (s, 1H); 6.20 (s, 1H); 6.9–7.4 (11H); 7.64 (t, J=6 Hz, 1H); 7.92 (s, 1H); 8.10(d, J=6 Hz, 1H); 8.22 (d, J=4 Hz, 1H); 8.47 (d, J=5 Hz, 1H); 9.05 (s, 1H).

EXAMPLE 18

4-(2-Chlorophenyl)-3-carboxy-6-methyl-2-[2-(2-methyl-1-imidazo-[4,5-c]pyridyl)ethoxymethyl]-5-[N-(2-pyridyl)carbamoyl]-1,4-dihydropyridine 3-Benzyloxycarbonyl-4-(2-chlorophenyl)-6-methyl-2-[2-(2-methyl-1-imidazo[4,5-c]pyridyl)ethoxymethyl]-5-[N-(2-pyridylcarbamoyl]-1,4-dihydropyridine (1.1 g) in ethanol (75 ml) was hydrogenated over 30% palladium on charcoal (0.75 g) at atmospheric pressure for 18 hours. The catalyst was filtered through arbacell and the filter pad washed with boiling ethanol (5×100 ml). The ethanol was removed under reduced pressure yielding the title compound as a foam (0.89 g; 94%).

N.M.R. (DMSO-d$_6$) δ: 1.80 (s, 3H); 2.63 (s, 3H); 3.88 (t, J=4 Hz, 2H); 4.35 (br, 1H); 4.52 (t, J=4 Hz, 2H); 4.60 (d, J=10 Hz, 1H); 4.68 (d, J=10 Hz, 1H); 5.33 (s, 1H); 7.0–7.2 (5H), 7.66 (m, 2H); 7.74 (s, 1H); 7.95 (d, J=6 Hz, 1H); 8.24 (m, 2H); 8.80 (s, 1H); 10.18 (s, 1H).

EXAMPLE 19

4-(2-Chlorophenyl)-3-N-ethylcarbamoyl-6-methyl-2-[2-(2-methyl-1-imidazo[4,5-c]pyridyl)ethoxymethyl]-5-[N-(2-pyridyl)carbamoyl]-1,4-dihydropyridine A suspension of 4-(2-chlorophenyl)-3-carboxy-6-methyl-2-[2-(2-methyl-1-imidazo[4,5-c]pyridyl)ethoxymethyl]-5-[N-(2-pyridyl)carbamoyl]-1,4-dihydropyridine (315 mg) in dry dichloromethane (6 ml) was treated with 4-dimethylaminopyridine (72 mg) and N,N-dicyclohexylcarbodiimide (140 mg). The suspension was stirred for 4 hours and ethylamine (635 mg) added. The reaction was stirred at room temperature for 18 hours. The solvent was removed under reduced pressure and the crude product chromatographed on silica eluting with a mixture of methanol, ethyl acetate and diethylamine 10:85:5. Fractions containing the product were evaporated and the resulting foam was sonicated in dietyl ether (10 ml) for 30 minutes. The ether was removed and the product dried under vacuum to yield the title compound as a yellow solid (65 mg, 20%).

N.M.R. (CDCl$_3$) δ1.04 (t, J=6 Hz, 3H); 1.84 (s, 3H); 2.74 (s, 3H); 3.20 (m, 2H); 3.94 (t, J=4 Hz, 2H); 4.47 (t, J=4 Hz, 2H); 4.80 (d, J=10 Hz, 1H); 4.90 (d, J=10 Hz, 1H); 5.22 (s, 1H); 5.88 (br, 1H); 6.08 (s, 1H); 7.0–7.2 (6H); 7.64 (m, 1H); 7.92 (br, 1H); 8.14 (d, J=6 Hz, 1H); 8.22 (d, J=4 Hz, 1H); 8.48 (d, J=5 Hz, 1H); 9.02 (s, 1H).

Preparation 1

3-(2-Hydroxyethyl)-2-methylimidazo[4,5-b]pyridine (a) 2-[2-Hydroxyethylamino]-3-aminopyridine 2-(2-Hydroxyethylamino)-3-nitropyridine (8.9 g) was dissolved in ethanol (200 ml) and hydrogenated over 5% palladium on charcoal (400 mg) at 50 p.s.i. (3.45 bar) for 2½ hours. The reaction mixture was filtered and the ethanol removed under reduced pressure, yielding the title compound (4.2 g, 56%) as a dark oil which was used without purification in 1(b) below.

(b) 3-(2-Hydroxyethyl)-2-methylimidazo[4,5-b]pyridine 2-(2-Hydroxyethylamino)-3-aminopyridine (3.4 g) was dissolved in acetic anhydride (140 ml) and stirred at reflux for 15 hours. The reaction mixture was cooled and the excess of reagent removed under reduced pressure. The dark brown oil was dissolved in ethanol (100 ml), 2N sodium hydroxide (50 ml) was added and the mixture was stirred for 15 minutes. The solution was acidified to pH5 using 2N hydrochloric acid and the solvents removed under reduced pressure. The residue was chromatographed over silica eluting with 10% methanol in ethyl acetate to yield the title compound (2.32 g, 59%) as a foam.

N.m.r. (CDCl$_3$) $\delta$2.67 (s, 3H); 4.13 (t, J=4 Hz, 2H); 4.38 (t, J=4 Hz, 2H); 5.50 (br, 1H); 7.04 (m, 1H); 7.68 (d, J=6 Hz, 1H); 8.20 (d, J=4 Hz, 1H).

Preparation 2

1-(2-Hydroxyethyl)-2-methylimidazo[4,5-c]pyridine

The title compound was prepared by the method of Preparation 1 starting with 4-[2-hydroxyethylamino]-3-nitropyridine.

N.m.r. (CD$_3$OD). $\delta$2.74 (s, 3H); 3.92 (t, J=6 Hz, 2H); 4.40 (t, J=6 Hz, 2H); 7.65 (d, J=5 Hz, 1H); 8.34 (d, J=5 Hz, 1H); 8.82 (s, 1H).

Preparation 3

3-(2-Hydroxyethyl)-2-methylimidazo[4,5-c]pyridine

2-Methylimidazo[4,5-c]pyridine (10.6 g) was mixed with ethylene carbonate (8.3 g) and heated as a melt at 150° C. for ½ hour. The crude black product was chromatographed on silica eluting with 40% methanol in ethyl acetate. The fraction with Rf 0.33 in methanol, ethyl acetate, (2:3) was evaporated and was identified as a mixture of the title compound and of the isomeric 1-(2-hydroxyethyl)-2-methylimidazo[4,5-c]pyridine.
The mixture was chromatographed on silica eluting with 20% methanol in acetone. Fractions containing the more mobile isomer were combined and evaporated yielding the title compound (1.22 g, 9%) as a foam.

N.M.R. (CD$_3$OD) $\delta$2.75 (s, 3H); 3.98 (t, J=6 Hz, 2H); 4.49 (t, J=6 Hz, 2H); 7.65 (d, J=5 Hz, 1H); 8.33 (d, J=5 Hz, 1H); 8.90 (s, 1H).

Preparation 4

2-(3-Hydroxypropyl)-1-methylimidazo[4,5-c]pyridine

3-Amino-4-methylaminopyridine (2.95 g), gamma-butyrolactol (2.53 g) and copper acetate (9.8 g) were suspended in a mixture of ethanol (100 ml) and water (100 ml) and heated in a sealed vessel at 150° C. for 4 hours. The reaction mixture was cooled and filtered. Hydrogen sulphide was bubbled through the solution for ½ hour, and after being stirred for a further ½ hour the precipitated copper sulphide was removed by filtration. The filtrate was neutralised with sodium bicarbonate and the solvents removed under reduced pressure. The crude product was chromatographed on silica eluting with 30% methanol in ethyl acetate. Fractions containing the product were combined and evaporated yielding the title compound. (1.95 g, 43%) as a foam.

N.M.R. (CD$_3$OD). $\delta$2.12 (m, 2H); 3.13 (t, J=5 Hz, 2H); 3.65 (t, J=5 Hz, 2H); 3.90 (s, 3H); 7.62 (d, J=4 Hz, 1H); 8.35 (d, J=4 Hz, 1H); 8.85 (s, 1H).

Preparation 5

3-(2-Hydroxyethyl)-2-methylimidazo[1,2-a]pyridine

2-Methylimidazo[1,2-a]pyridyl-3-acetic acid (190 mg) was added in portions to a stirred suspension of lithium aluminium hydride (57 mg) in dry tetrahydrofuran (5 ml) under nitrogen. The mixture was heated at reflux temperature for 2 hours then cooled and the reaction quenched by the careful addition of water (60 $\mu$l) followed by 2N sodium hydroxide solution (200 $\mu$l) and water (100 $\mu$l). Methanol (20 ml) was added and the slurry was filtered. The filtrate was evaporated and the residue chromatographed on silica eluting with ethyl acetate containing 20% methanol to give the title compound (65 mg, 37%).

N.M.R. (CDCl$_3$) $\delta$2.38 (s, 3H); 3.13 (t, J=4 Hz, 2H); 3.92 (t, J=4 Hz, 2H); 6.75 (t, J=5 Hz, 1H); 7.05 (t, J=5 Hz, 1H); 7.34 (d, J=5 Hz, 1H); 8.04 (d, J=5 Hz, 1H).

Preparation 6

1-(2-Hydroxyethyl)-2-methylimidazo[4,5-b]pyridine (a) Acetoxyacetyl chloride (2.73 g, 20 mmol) was added dropwise to a stirred solution of imidazole (2.72 g, 40 mmol) in dry tetrahydrofuran (20 ml) under nitrogen at 0° C. After the addition was complete, the thick white suspension was cooled to −78° C. and a solution of 2,3-diaminopyridine (2.18 g, 20 mmol) in dry tetrahydrofuran (60 ml) was added over 10 minutes. The mixture was allowed to warm to room temperature overnight and then saturated aqueous sodium bicarbonate (100 ml) was added. The mixture was extracted with dichloromethane (3×80 ml), the extracts were dried (MgSO$_4$) and concentrated under reduced pressure to give a brown solid. Recrystallisation from ethyl acetate gave 3-(acetoxyacetyl)amino-2-aminopyridine (795 mg, 38%) as white flakes.

(b) Lithium aluminium hydride (2.81 g, 74 mmol) was added in portions to a stirred solution of the above product in dry tetrahydrofuran (100 ml) under nitrogen at 0° C. The mixture was then stirred at room temperature for 18 hours and the quenched with 20% aqueous sodium hydroxide (200 ml). The resulting mixture was continuously extracted with dichloromethane (1.5 liters) for 20 hours. The dichloromethane solution was dried (MgSO$_4$) and concentrated under reduced pressure. The resulting brown solid was purified by flash chromatography (eluting with ethyl acetate/methanol, 3:1) to give 2-amino-3-(2-hydroxyethylamino)-pyridine (1.268 g, 56%), as a brown solid.

(c) A mixture of the above product (1.268 g, 8.3 mmol) and acetic anhydride (40 ml) was heated at 125° C. for 5 hours. The excess reagent was removed under reduced pressure, and the residual oil was dissolved in a mixture of concentrated aqueous ammonia (25 ml) and methanol (25 ml). After 2 hours the solution was concentrated, and the residue was purified by flash chromatography (eluting with ethyl acetate/methanol, 3:1) and a second time (eluting with ethyl acetate/methanol/diethylamine, 85:10:5) to give 1-(2-hydroxyethyl)-2-methylimidazo[4,5-b]-pyridine (545 mg, 37%) as a white solid.

N.M.R. (CDCl$_3$) $\delta$: 2.56 (3H, s), 4.19 (2H, m), 4.30 (2H, m), 6.57 (1H, brs), 6.89 (1H, dd, J 3 and 8 Hz), 7.51 (1H, d, J 8 Hz), 8.01 (1H, d, J 3 Hz).

Preparation 7

3-(2-Hydroxyethyl)-2-methylimidazo[4,5-d]pyrimidine (a) 2-(5-Amino-6-chloro-4-pyrimidinylamino)ethanol (Chem. Pharm. Bull., 1961, 9, 27) (5.71 g, 30.3 mmol) and acetic anhydride (50 ml) were heated together under nitrogen at 120° C. for 20 hours. The excess reagent was removed under reduced pressure and the residue was neutralised with aqueous sodium bicarbonate and extracted with dichloromethane (4×70 ml). The extracts were dried (MgSO$_4$) and concentrated under reduced pressure. The residue was purified by flash chromatography (eluting with ethyl acetate) to give 3-(2-acetoxyethyl)-2-methyl-7-chlorimidazo-[4,5-d]pyrimidine (1.597 g, 21%), as a white solid.

(b) The above product (1.59 g, 6.24 mmol) was hydrogenated over 5% palladium on carbon (0.32 g) in a mixture of methanol (50 ml) and 3% aqueous ammonia (50 ml) at 30 p.s.i. (2 bar) and 20° C. for 1 hour. The mixture was filtered through Arbacel, and the filter cake was washed with boiling ethanol (50 ml). The filtrate was concentrated under reduced pressure, then passed through a short plug of silica gel eluting with ethyl acetate/methanol (3:2) to give 3-(2-hydroxyethyl)-2-methylimidazo[4,5-d]pyrimidine (1.10 g, 100%), as a white solid.

N.M.R. (CDCl$_3$) δ2.75 (3H, s), 3.80 (1H, brs), 4.13 (2H, brs), 4.23 (2H, t, J 5 Hz), 8.87 (1H, s), 8.90 (1H, s).

We claim:

1. A compound of the formula

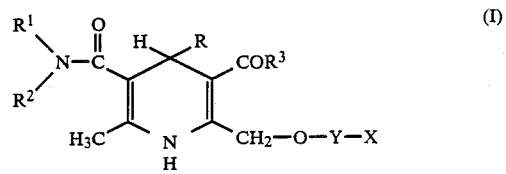

(I)

or a pharmaceutically acceptable salt thereof, wherein R is 2-chlorophenyl, 2-bromophenyl or 2-methylthiophenyl; $R^1$ is pyridyl or alkyl having one to four carbon atoms; $R^2$ is hydrogen; $R^3$ is alkoxy having one to four carbon atoms, benzyloxy, hydroxy or alkylamino having one to four carbon atoms; Y is ethylene or propylene; and X is 1-, 2- or 3-imidazopyridyl or 1-, 2- or 3-imidazopyrimidyl optionally substituted by methyl.

2. A compound of claim 1, wherein R is 2-chlorophenyl; $R^2$ is hydrogen; $R^3$ is alkoxy having one to four carbon atoms; and Y is ethylene.

3. The compound of claim 2 wherein $R^1$ is t-butyl; $R^3$ is ethoxy; and X is 2-methyl-1-imidazo[4,5-c]pyridyl.

4. The compound of claim 2, wherein $R^1$ is 2-pyridyl; $R^3$ is ethoxy; and X is 2-methyl-1-imidazo[4,5-c]pyridyl.

5. A method for treating an inflammatory or allergic reaction in a mammal which comprises administering to said mammal an antiinflammatory or antiallergic effective amount of a compound according to claim 1.

6. A pharmaceutical composition useful for treating an inflammatory or allergic reaction in a mammal comprising a unit dosage form of a compound according to claim 1 together with a pharmaceutically acceptable diluent or carrier.

* * * * *